United States Patent [19]

Karube et al.

[11] Patent Number: 5,556,775
[45] Date of Patent: Sep. 17, 1996

[54] METHOD OF PRODUCING β-CYCLODEXTRIN

[75] Inventors: Isao Karube, Kawasaki; Nobuyuki Yoshida, Tokyo, both of Japan

[73] Assignees: Akebono Brake Industry Co., Ltd., Tokyo; Akebono Research and Development Center, Ltd., Saitama, both of Japan

[21] Appl. No.: 211,920

[22] PCT Filed: Aug. 25, 1993

[86] PCT No.: PCT/JP93/01193

§ 371 Date: Jun. 22, 1994

§ 102(e) Date: Jun. 22, 1994

[30] Foreign Application Priority Data

Aug. 25, 1992 [JP] Japan ..................................... 4-226156

[51] Int. Cl.⁶ ....................................................... C12P 19/18
[52] U.S. Cl. ............................. 435/97; 536/103; 536/124
[58] Field of Search ..................................... 536/103, 124; 435/97

[56] References Cited

U.S. PATENT DOCUMENTS

| | | | |
|---|---|---|---|
| 3,425,910 | 2/1969 | Armbruster et al. | 435/97 |
| 3,640,847 | 2/1972 | Armbruster et al. | 195/31 R |
| 3,812,011 | 5/1974 | Okada et al. | 435/97 |
| 4,135,977 | 1/1979 | Horikoshi et al. | 435/97 |
| 4,477,568 | 10/1984 | Hokse et al. | 435/97 |
| 5,326,701 | 7/1994 | Shieh et al. | 435/97 |

OTHER PUBLICATIONS

Szejtli "Cyclodextrins and their Inclusion Complexes" pp. 66–73 (1982).

*Primary Examiner*—Jeffrey Mullis
*Attorney, Agent, or Firm*—Knobbe, Martens, Olson & Bear

[57] ABSTRACT

The present invention; is a method of producing β-cyclodextrin at a higher efficiency from a raw material other than starch, comprising making a malto-oligosaccharide with 2 to 10 glucoses co-exist with cyclodextrin glucanotransferase in a solution containing an organic solvent which can precipitate 50% or more of β-cyclodextrin when an excessive amount of the solvent is added to the solution of the β-cyclodextrin and effecting the reaction at a lower temperature than 40° C.

6 Claims, 6 Drawing Sheets

METHOD OF PRODUCING β-CYCLODEXTRIN

TECHNICAL FIELD

The present invention relates to a method of producing cyclodextrin. More specifically, the present invention relates to a method of producing β-cyclodextrin at a higher efficiency from a raw material excluding starch.

BACKGROUND ART

Cyclodextrin; hereinafter refered to as "CD", is a nonreducing malto-oligosaccharide where 6 to 12 glucoses are bonded together in a cyclic form via glucoside bonding. For industrial CD production, α-CD with six glucoses bonded together, β-CD with seven glucoses bonded together, and γ-CD with eight glucoses bonded together, are produced as a single product or a mixture thereof.

CD, an amphoteric substance having the hydrophilic outer ring circumference and also having the hydrophobic pore, has an inclusion function to stably include a variety of molecules and the like in the hydrophobic pore.

Therefore, CD potentially prepares volatile matters into non-volatile matters or provides masking of unpleasant odor, so CD is applicable in a wide variety of fields, for example, for use in medicinal products, foodstuffs, cosmetics and the like.

CD has conventionally been produced via an enzyme reaction, ie. the reaction of a CD generating enzyme (cyclodextrin glucanotransferase; hereinafter referred to as "CGTase") with starch as a substrate. The substrate concentration should preferably be higher from industrial point, which involves the increase in the viscosity of the reaction solution whereby the stirring procedure gets hard along with a lower reaction rate. Thus, a method has been proposed, comprising preliminarily subjecting starch to the pretreatment process with α-amylase for liquidation to decrease the viscosity, but the process is complex.

Because the reaction product is produced as a mixture of CDs of α, β, and γ type, purification is needed so as to obtain β-CD for primary use, and thus, the decrease of the yield is unavoidable. Alternatively, no report has been issued of the CD production via CGTase using a substrate other than starch.

The present invention has been undertaken from such respect. The objective of tile present invention is to provide a method of producing β-CD with a substrate other than starch at a higher efficiency.

DISCLOSURE OF THE INVENTION

The present inventors have made intensive investigations so as to achieve the above objective. Consequently, the inventors have found that the production of β-CD alone can be achieved by using a malto-oligosaccharide of a higher concentration as a raw material substrate followed by the reaction with CGTase.

That is, the present invention is a method of producing β-cyclodextrin comprising steps of making a malto-oligosaccharide with 2 to 10 glucoses co-exist with cyclodextrin glucanotransferase in a solution containing an organic solvent which can precipitate 50% or more of β-cyclodextrin when an excessive amount of the solvent is added to the solution of the β-cyclodextrin and effecting the reaction at a lower temperature than 40° C.

The present invention will now be explained in details.

The process of producing the CD in accordance with the present invention is characterized in that CGTase effects on such malto-oligosaccharide in the presence of the organic solvent.

Such malto-oligosaccharide as the raw material substrate is preferably those of a polymerization degree of 2 to 10, and these may be used singly or in a mixture thereof. Maltose is specifically preferable in terms of ready availability and production cost.

As CGTase, use is made of the enzymes which are generated from *Bacillus macerans, Bacillus megaterium, Bacillus circulans* and the like and which are to be used generally for industrial CD production. However, these enzymes catalyze various reactions, in accordance with the present invention, β-CD is generated via intramolecular conversion (cyclization) or intermolecular conversion (disproportionation).

Preferably, such organic solvent forms an inclusion compound together with β-CD relatively strongly, illustratively including one of cyclic hydrocarbons such as cyclohexane, cyclooctane, cyclododecane and the like, aromatic hydrocarbons such as benzene, ethyl benzene, o-xylene, m-xylene, p-xylene, o-dichlorobenzene, naphthalene, anthracene and the like, halogen compounds such as tetrachloroethylene, chloroform and the like; or a mixture of two or more thereof. Among then, cyclohexane is specifically preferable.

The organic solvent in the reaction solution is preferably at a concentration of 30 to 80 vol %, more preferably 40 to 60 vol %, and is mixed and stirred with water or a buffer for the reaction.

When maltose is used as the substrate, the yield of β-CD reaches maximum when the substrate concentration is at 40 w/v % and it does not increase even if the concentration is more than 40 w/v %, so the synthesis should preferably be done in a range below the concentration in terms of yield. Similarly, the yield moves toward maximum around 60 hours after the initiation of the reaction. When the reaction period is far longer than 60 hours, the yield is lowered. Thus, the reaction should be carried out for 60 hours or less. Also, pH of the reaction solution is preferably 4.5 to 8, more preferably 5 to 7.

The optimum temperature of CGTase is around 50 C, but if the reaction is carried out at a temperature above 40° C., CD is not generated. Therefore, the reaction should be carried out at a temperature lower than 40° C., preferably at 25° C. or less, more preferably at 10° C. or less.

Because the generated β-CD precipitates after the formation of an inclusion compound together with the organic solvent, the β-CD can readily be separated from the reaction solution and unreacted substrate.

When CGTase effects on a malto-oligosaccharide, the malto-oligosaccharide is modified via intramolecular conversion into a malto-oligosaccharide of nearly glucose monomer to glucose octamer (malto-octanose). Herein, an oligosaccharide of not less than glucose hexamer is possibly modified into CD via intramolecular conversion. Because the malto-oligosaccharide is also present simultaneously in the system, however, the generated CD is rapidly degraded via ring-opening conversion so that almost no CD remains in the system.

If the reaction is carried out in a system with the organic solvent added to generate the precipitate of the reaction product after the formation of an inclusion compound with CD, the CD generated via cyclization is hardly exposed to the enzyme action and is therefore accumulated in the reaction system.

In accordance with the present invention, furthermore, CD is generated via the reaction at 40° C. or less, which is supposed due to the fact that an inclusion compound of CD with an organic solvent is present in more stable manner when the temperature is set at 40° C. or less.

BRIEF DESCRIPTION OF THE DRAWINGS

in FIG. 1A cyclohexane was not added; in FIG. 1B cyclohexane was added.

in FIG. 1A cyclohexane was not added; in FIG. 1B, cyclohexane was added.

BEST MODE FOR CARRYING OUT THE INVENTION

The examples of the present invention will now be described in details. In the following examples, the CGTase (product name; Contizyme derived from *Bacillus macerans*, commercially available from Amano Pharmaceuticals, Co. Ltd.) was used at 300 U (in Tilden-Hudson Unit: J. Bacteriol. 43, 527(1942)) per gram substrate. The enzyme primarily generates α-CD when starch is employed as the substrate.

For the analysis of the reaction products, use was made of glucoamylase, derived from *Rizopus niveus* and commercially available from Seikagaku Kogyo, Co. Ltd.

EXAMPLE 1

Explanation will follow of CD production in a cyclohexane-water system, using maltose as a substrate.

CD synthesis was performed in 0.5 ml of 50 mM acetate buffer (pH 5.2) with various amount of cyclohexane. Under stirring at 7.5° C., the reaction was continued at a 20% substrate concentration for 66 hours.

The reaction products were analyzed by HPLC (high-performance liquid chromatography) on a column, ASAHIPAK NH2P-50 (manufactured by Asahi Kasei, Co. Ltd.).

Figure 1A:
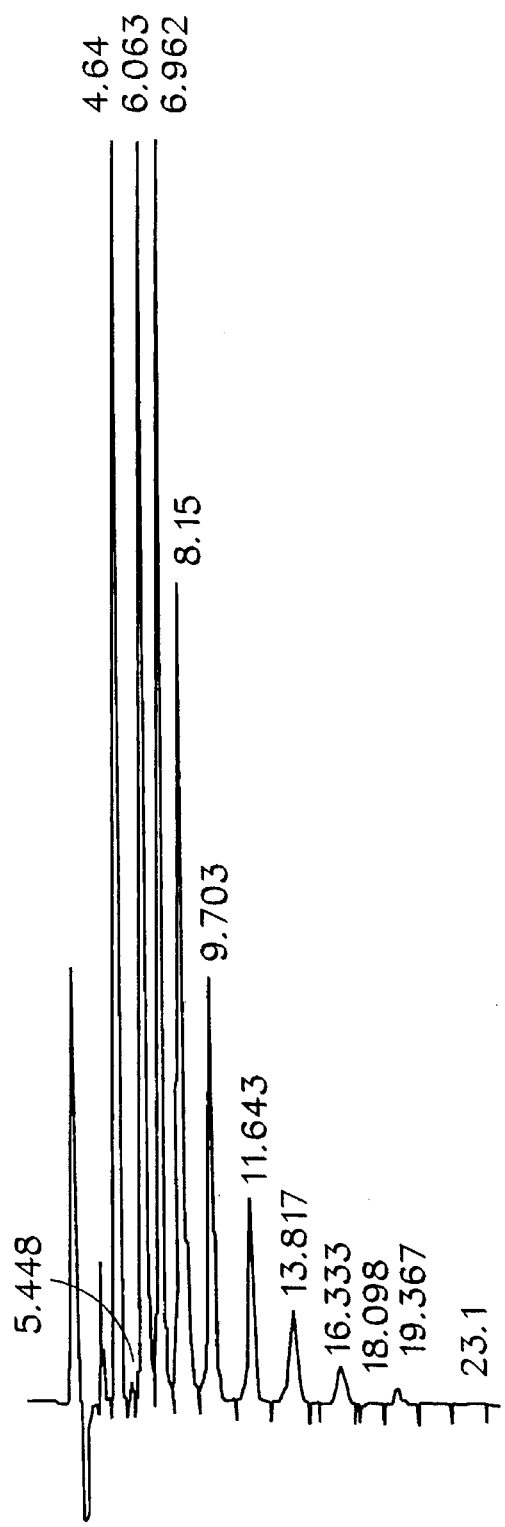
FIGS. 1A and 1B show the chromatograms of the products by β-CD synthesis.
Figure 1B:
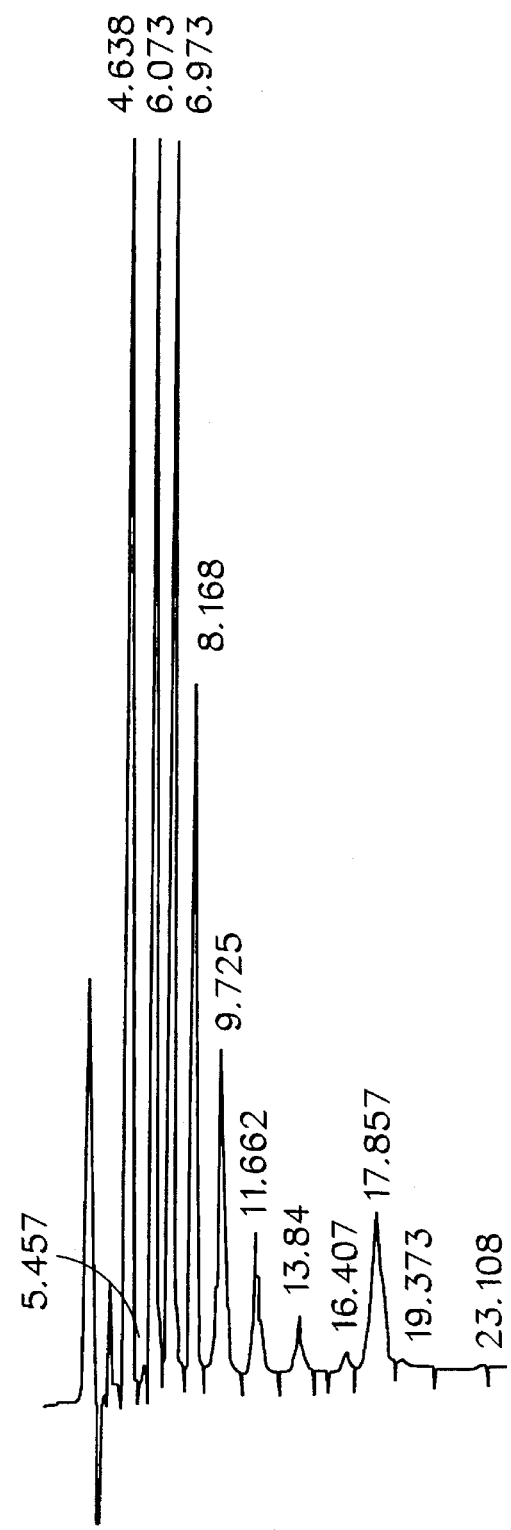
Figure 2A:
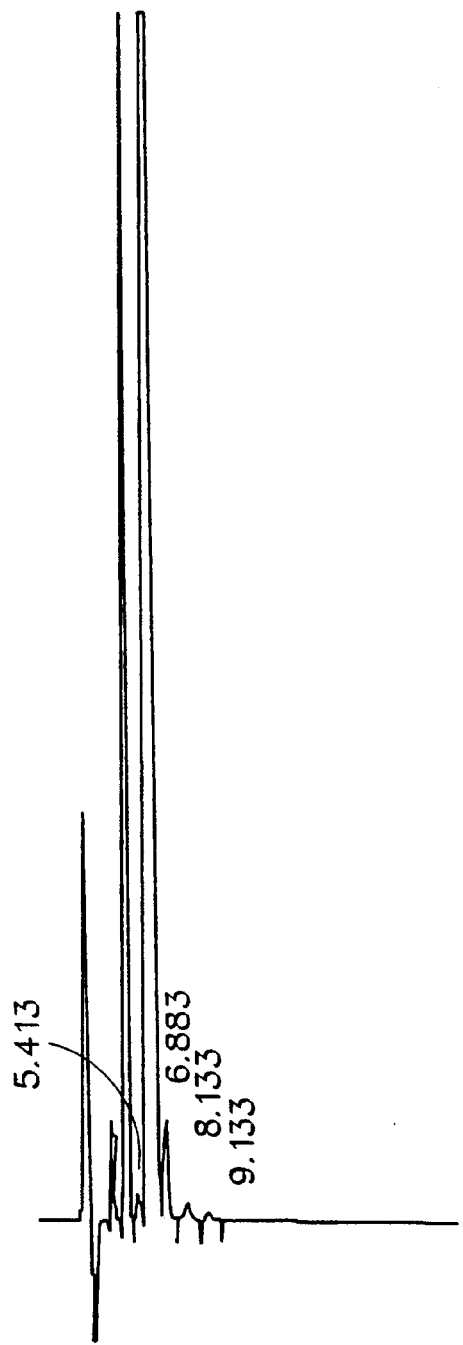
FIGS. 2A and 2B show the chromatograms of the products by β-CD synthesis after glucoamylase treatment.
Figure 2B:
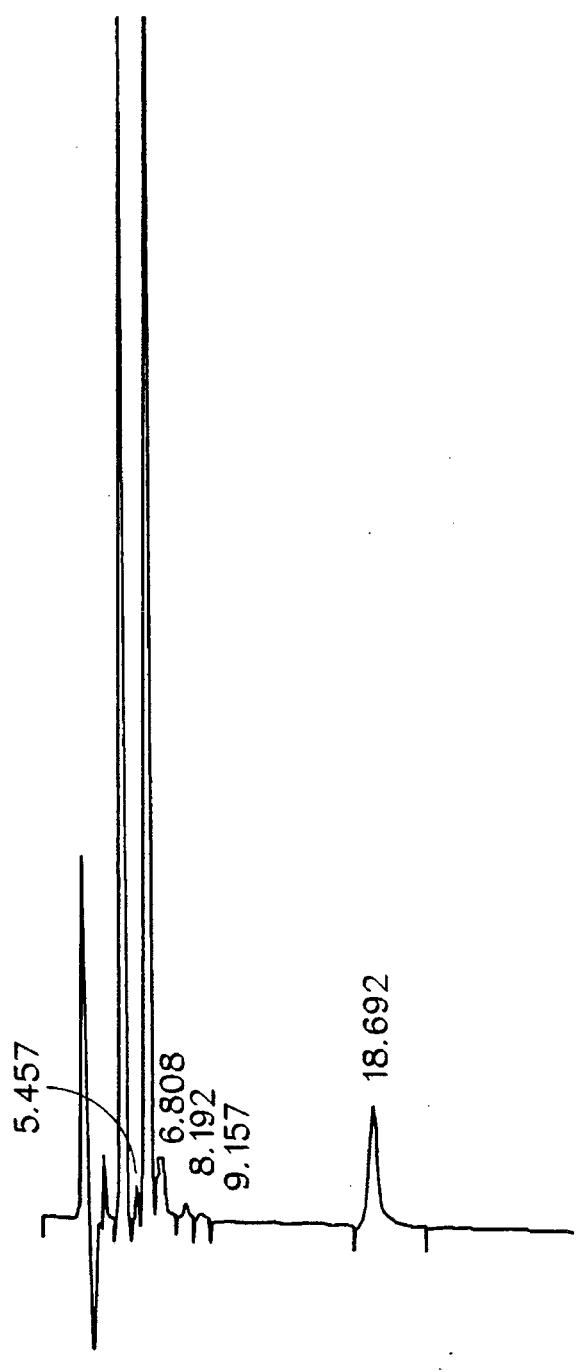
Figure 2C:
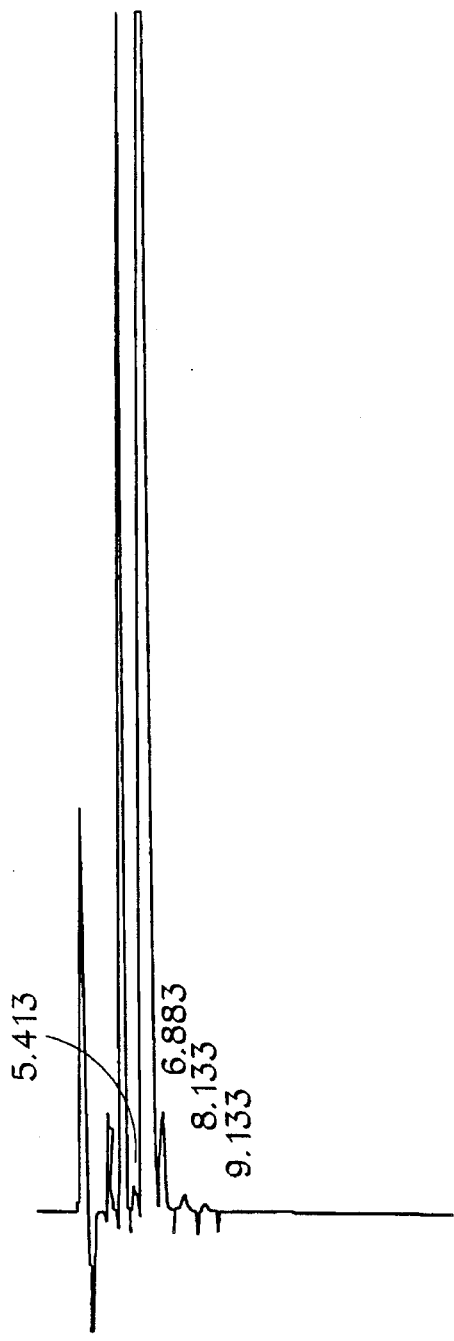
Figure 2D:
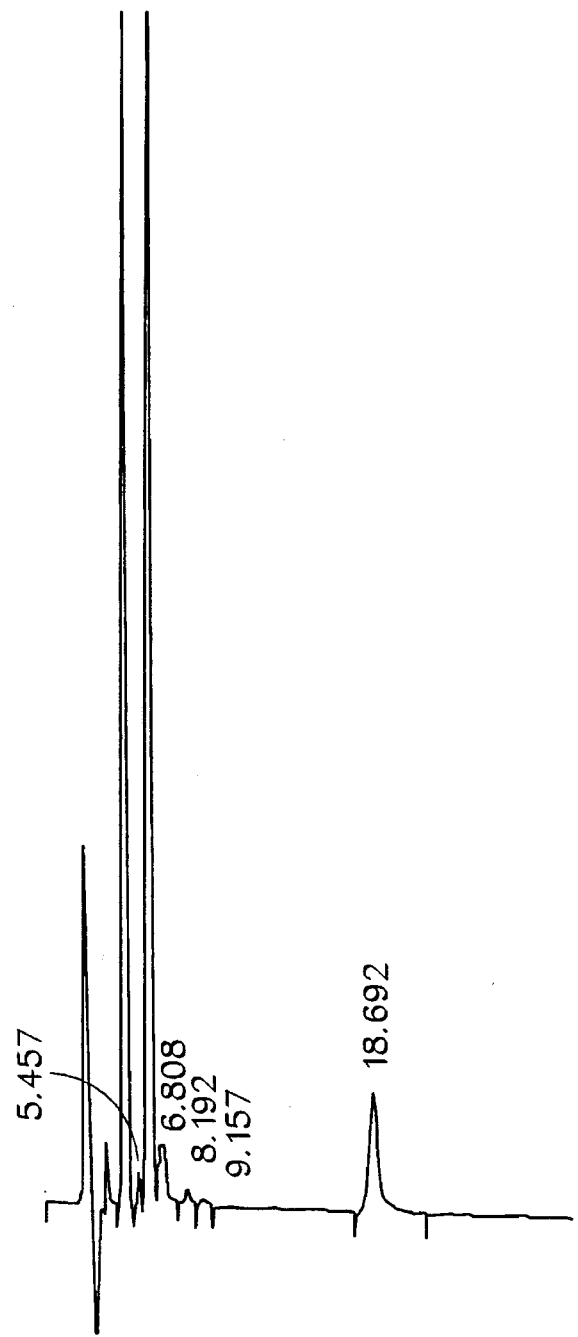

FIG. 1 shows the chromatograms of the reaction products with no cyclohexane added (A) and with 0.4 ml of cyclohexane added (B). At a 17.857-min position of B, a peak was observed, which was not observed in A. The peak has the same retention time as that of the standard β-CD.

FIG. 2 shows the chromatograms of the reaction products after glucoamylase was added to these products to decompose linear malto-oligosaccharide. Herein, CD is not decomposed with glucoamylase. The peak corresponding to the standard β-CD remains in D. These results indicate that the peak is that of β-CD.

Figure 3:
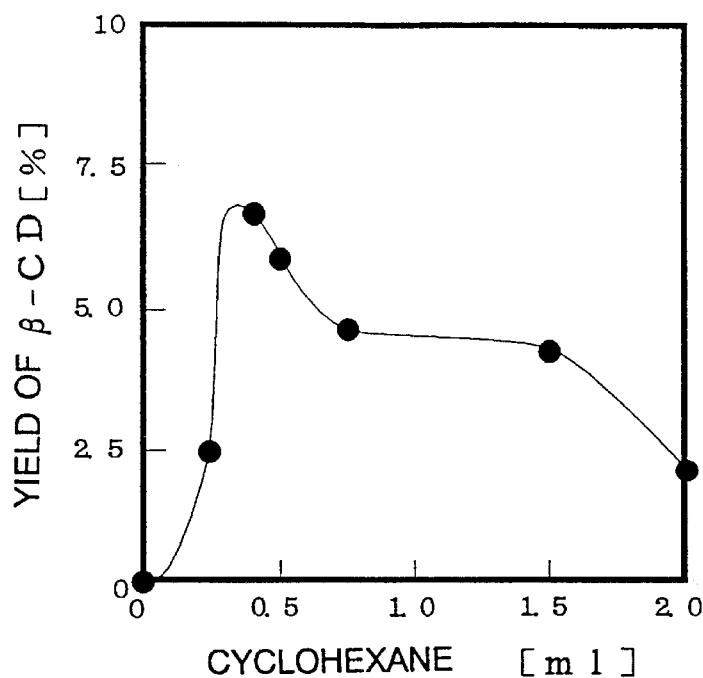
FIG. 3 is a graph depicting the relation between the amount of cyclohexane in the reaction solution and the yield of β-CD.
Figure 4:
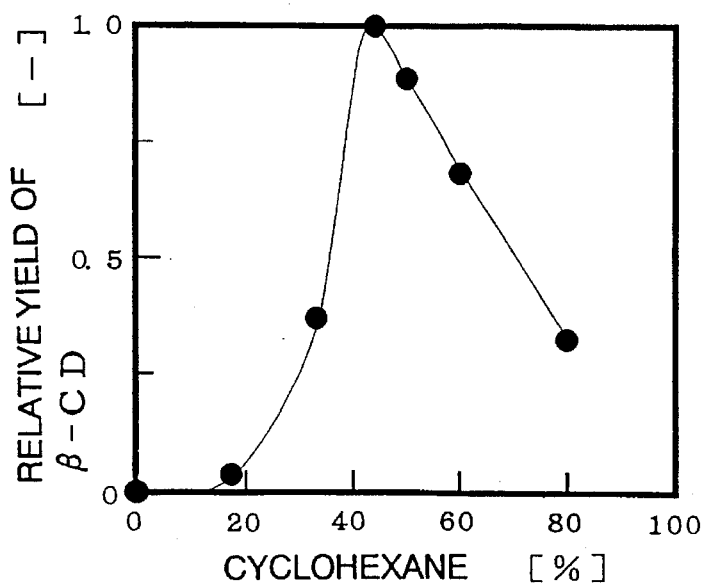
FIG. 4 is a graph depicting the relation between the cyclohexane concentration and the relative yield of β-CD.

FIG. 3 shows the calculated yield (%) of β-CD in the individual reactions when the peak area described above was used as an indicator. FIG. 4 shows the yield of β-CD relative to the cyclohexane concentration (cyclohexane volume % to the total volume of the reaction solution) when the maximum yield of β-CD was defined as 1.0.

These results indicate that β-CD is generated, by using maltose as the substrate through the reaction of CGTase in a cyclohexane-water system. Also, it is indicated that the cyclohexane concentration is preferably 30 to 80%, more preferably 40 to 60%.

EXAMPLE 2

Examination was then done about solvents to be used in accordance with the present invention. To 1% solutions each of α-CD, β-CD and γ-CD, an organic solvent was added at an excess amount followed by stirring for several minutes at room temperature for HPLC analysis of the supernatant of the aqueous phase so as to determine the amount of the precipitate. The solvent in which α-CD, β-CD or γ-CD was absolutely precipitated was designated as a solvent of 100% precipitation ratio. Those solvents which were solid at room temperature were dissolved in hexane for use.

As in Example 1, similar reactions were effected when each of the solvents was adjusted to a concentration of 44.4%. The analysis was done of the presence or absence of precipitate during the reaction and of the precipitate per se, if any. The results are shown in Table 1.

TABLE 1

| Organic solvent | Precipitation ratio | | | Precipitate during reaction |
|---|---|---|---|---|
| | α-CD | β-CD | γ-CD | |
| Hexane | 39.2 | 50.9 | 17.9 | x |
| Decane | 49.0 | 14.1 | 11.6 | x |
| Dodecane | 60.7 | 25.8 | 17.1 | x |
| Tridecane | 62.8 | 16.2 | 17.2 | x |
| Hexadecane | 69.5 | 19.2 | 17.8 | x |
| Cyclohexane | 84.1 | 94.0 | 0 | β - C D |
| Cyclooctane | 8.7 | 56.4 | 20.0 | β - C D |
| Benzene | 11.1 | 87.5 | 11.8 | β - C D |
| Ethyl benzene | 13.3 | 93.3 | 94.9 | β - C D |
| o-Xylene | 0 | 97.7 | 96.6 | β - C D |
| m-Xylene | 0 | 93.8 | 88.6 | β - C D |
| p-Xylene | 10.1 | 96.7 | 27.0 | β - C D |
| o-Dichlorobenzene | 5.3 | 98.9 | 99.2 | β - C D |
| Tetrachloroethylene | 8.0 | 98.4 | 93.9 | β - C D |
| Chloroform | 2.1 | 89.5 | 92.2 | β - C D |
| Cyclododecane + Hexane | 35.7 | 91.0 | 0 | β - C D |
| Naphthalene + Hexane | 55.4 | 99.5 | 85.5 | β - C D |
| Anthracene + Hexane | 34.0 | 90.8 | 0 | β - C D |

These results indicate that β-CD can be generated by the use of an organic solvent capable of precipitating about 50% or more of β-CD.

Figure 5:
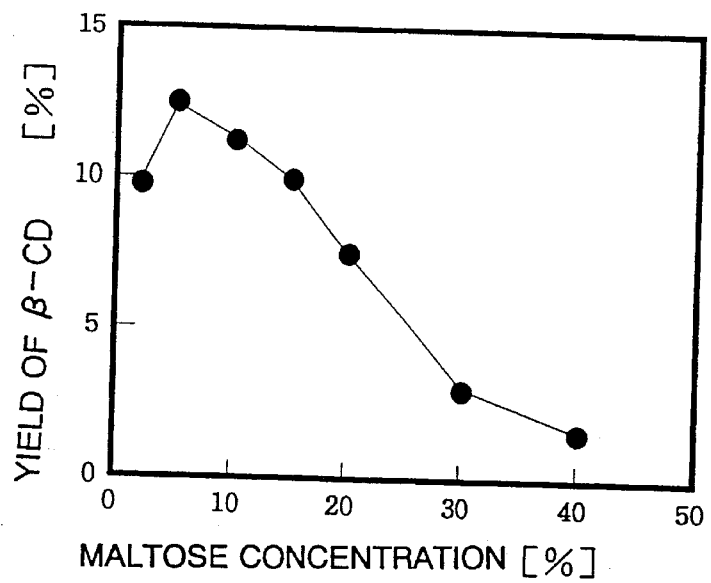
FIG. 5 is a graph depicting the relation between the substrate concentration and the yield of β-CD.

EXAMPLE 3

β-CD was synthesized under various concentrations of substrate. The enzyme was maintained at a constant level (300 U/g) relative to the weight of the substrate. Cyclohexane (44.4%) was used as an organic solvent, for carrying out the reaction for 48 hours under the same conditions as in Example 1. The results are shown in FIG. 5.

The results indicate that the elevation of the maltose concentration increases the yield of β-CD. However, the yield reaches plateau when the concentration is above 30%.

EXAMPLE 4

Figure 6:
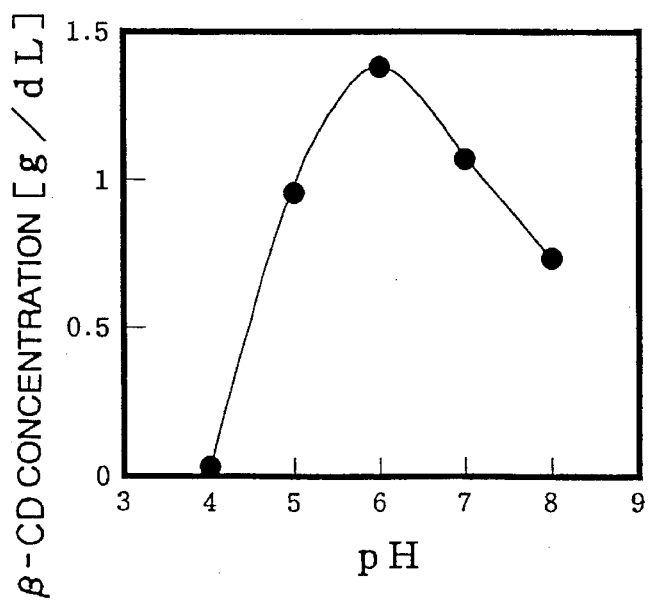
FIG. 6 is a graph depicting the effect of pH on the synthesis of β-CD.

Examination was done about the effect of pH on the β-CD synthesis using as a substrate maltose (20%). Cyclohexane (44.4%) was used as an organic solvent; as a buffer, 50 mM acetate buffer was used at pH 4 to 5 while at pH 6 to 8, 50 mM phosphate buffer was used. The results are shown in FIG. 6.

These results indicate that the preferable pH is pH 5 to 8.

EXAMPLE 5

Furthermore, examination was done about the relation between the reaction time and the yield of β-CD in the β-CD synthesis.

Figure 7:
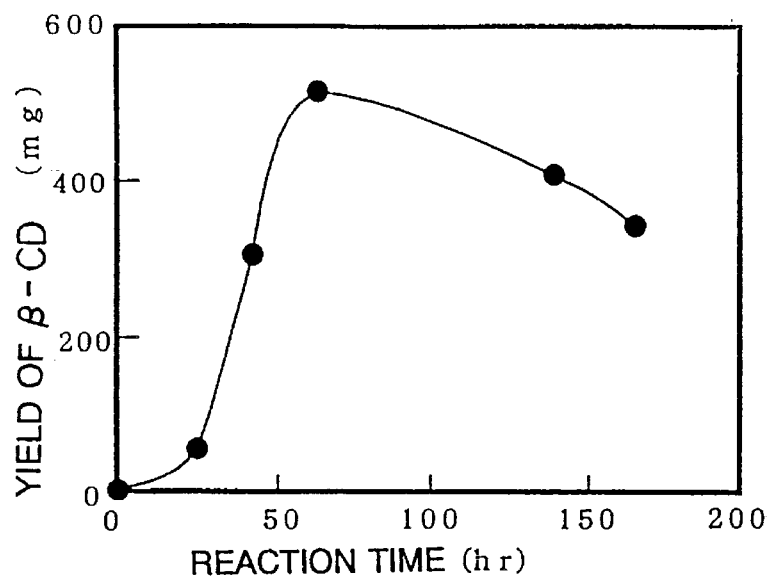
FIG. 7 is a graph depicting the relation between the yield of β-CD and the reaction time.

Using maltose (20%) as a substrate, the reaction was effected at 7.5° C. in a mixture of 30 ml of cyclohexane and 24 ml of 100 mM acetate buffer (pH 6.0). The results are shown in FIG. 7.

The results indicate that the CD yield reached maximum around 60 hours after the initiation from the reaction, and that the yield was gradually lowered thereafter.

EXAMPLE 6

Figure 8:
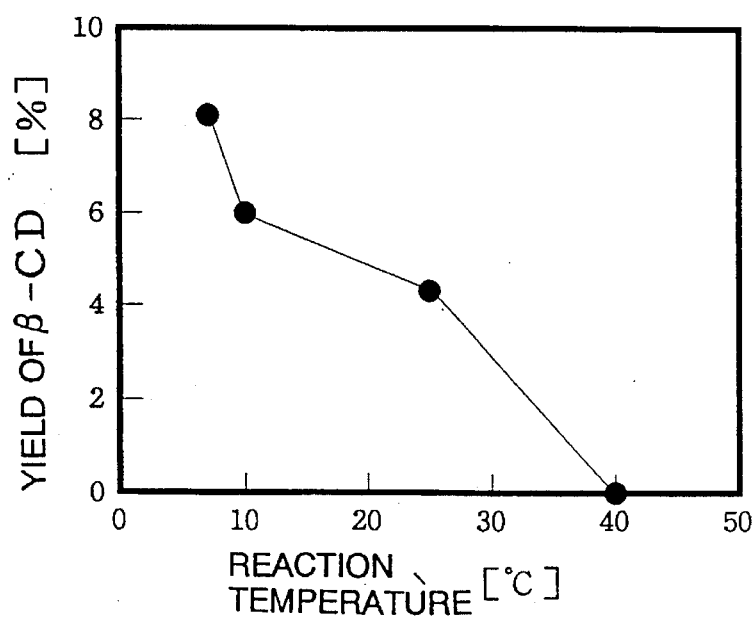
FIG. 8 is a graph depicting the relation between the yield of β-CD and the reaction temperature.

The effect of temperature on the β-CD synthesis was examined. Using as a substrate maltose (20%) and as an organic solvent cyclohexane (44.4%), the reaction was effected in a mixture of 50 mM phosphate buffer and the organic solvent at various temperatures for 48 hours. The results are shown in FIG. 8.

The results indicate that no synthesis of β-CD occurred at 40° C. but that such reaction occurred at a temperature less than 40° C.

INDUSTRIAL APPLICABILITY

In accordance with the present invention, the production of β-CD from the raw material other than starch is realized. In accordance with the present method, the viscosity of the reaction solution is not elevated even when the raw material is at a higher concentration. Thus, no pretreatment thereof is required. Because the reaction product is β-CD alone, the purification procedure is simple.

We claim:

1. A method of producing β-cyclodextrin, comprising the steps of:

enzymatically converting a substrate consisting essentially of maltose into β-cyclodextrin, using cyclodextrin glucanotransferase, in a solution containing 30 to 80 vol % of an organic solvent, at a temperature lower than 40° C., at a pH and for a time sufficient to generate β-cyclodextrin, said organic solvent capable of precipitating 50% or more of β-cyclodextrin if added to a solution containing β-cyclodextrin, wherein only β-cyclodextrin is substantially generated and precipitated in the solution such that any generated β-cyclodextrin is substantially degraded in the absence of said solvent; and recovering the precipitated β-cyclodextrin from the solution.

2. A method according to claim 1, wherein said solution contains 40 to 60 vol % of the organic solvent.

3. A method according to claim 1, wherein said pH is in the range of 5–8.

4. A method of producing β-cyclodextrin, comprising the steps of:

enzymatically converting a substrate of malto-oligosaccharide into β-cyclodextrin, using cyclodextrin glucanotransferase, in a solution containing 30 to 80 vol % of an organic solvent, at a temperature of 10° C. or lower, at a pH and for a time sufficient to generate β-cyclodextrin, said organic solvent capable of precipitating 50% or more of β-cyclodextrin if added to a solution containing β-cyclodextrin, said malto-oligosaccharide having 2 to 10 glucose monomers such that any generated β-cyclodextrin is substantially degraded in the absence of said solvent in the absence of said organic solvent, wherein only β-cyclodextrin is substantially generated and precipitated in the solution; and recovering the precipitated β-cyclodextrin from the solution.

5. A method according to claim 4, wherein said malto-oligosaccharide is maltose.

6. A method according to claim 1 or 5, wherein the organic solvent is selected from the group consisting of cyclohexane, cyclooctane, benzene, ethyl benzene, o-xylene, m-xylene, p-xylene, o-dichlorobenzene, tetrachloroethylene, chloroform, cyclododecane, naphthalene and anthracene.

\* \* \* \* \*